United States Patent
Kennedy

(10) Patent No.: US 7,357,808 B2
(45) Date of Patent: Apr. 15, 2008

(54) SINGLE USE DEVICE FOR BLOOD MICROSAMPLING

(75) Inventor: Gwenn E. Kennedy, Ellenwood, GA (US)

(73) Assignee: Facet Technologies, LLC, Kennesaw, GA (US)

( * ) Notice: Subject to any disclaimer, the term of this patent is extended or adjusted under 35 U.S.C. 154(b) by 747 days.

(21) Appl. No.: 10/350,395

(22) Filed: Jan. 23, 2003

(65) Prior Publication Data
US 2003/0144609 A1    Jul. 31, 2003

Related U.S. Application Data
(60) Provisional application No. 60/353,917, filed on Jan. 31, 2002.

(51) Int. Cl.
*A61B 17/32*    (2006.01)
(52) U.S. Cl. ....................... 606/181; 600/583
(58) Field of Classification Search ................ 606/172, 606/181, 182, 183; 600/583; 604/136, 137, 604/156, 157, 411
See application file for complete search history.

(56) References Cited

U.S. PATENT DOCUMENTS

| | | | |
|---|---|---|---|
| 1,135,465 A | 4/1915 | Pollock | |
| 4,360,016 A | 11/1982 | Sarrine | |
| 4,388,925 A | 6/1983 | Burns | |
| 4,416,279 A | 11/1983 | Lindner et al. | |
| 4,503,856 A | 3/1985 | Cornell et al. | |
| 4,517,978 A | 5/1985 | Levin et al. | |
| 4,627,445 A | 12/1986 | Garcia et al. | |
| 4,858,607 A * | 8/1989 | Jordan et al. | 606/182 |
| 4,869,249 A * | 9/1989 | Crossman et al. | 606/182 |
| 4,924,879 A | 5/1990 | O'Brien | |
| 4,976,724 A | 12/1990 | Nieto et al. | |
| 5,279,294 A | 1/1994 | Anderson et al. | |
| 5,304,193 A | 4/1994 | Zhadanov | |
| 5,318,584 A | 6/1994 | Lange et al. | |
| 5,324,303 A | 6/1994 | Strong et al. | |
| 5,356,420 A | 10/1994 | Czernecki et al. | |
| 5,368,047 A | 11/1994 | Suzuki et al. | |
| 5,454,828 A | 10/1995 | Schraga | |
| 5,464,418 A | 11/1995 | Schraga | |

(Continued)

FOREIGN PATENT DOCUMENTS

DE    10057832 C1    2/2002

(Continued)

OTHER PUBLICATIONS

Bayer, "Ames Glucolet" lancing device; 2 pgs.

(Continued)

*Primary Examiner*—Michael J. Hayes
*Assistant Examiner*—Victor Nguyen
(74) *Attorney, Agent, or Firm*—Gardner Groff Greenwald & Villanueva, PC

(57) ABSTRACT

A lancing device including a spring-driven lancet translationally mounted within a housing. The lancet has at least one resilient finger extending outwardly therefrom and engageable within a cooperating recess formed in the housing to prevent re-use of the lancing device. A depth-adjustment knob is optionally included for contacting the housing to limit the travel of the lancet and thereby control the depth of penetration.

22 Claims, 3 Drawing Sheets

U.S. PATENT DOCUMENTS

| | | |
|---|---|---|
| D369,864 S | 5/1996 | Petersen |
| 5,554,166 A | 9/1996 | Lange et al. |
| 5,569,287 A | 10/1996 | Tezuka et al. |
| 5,613,978 A | 3/1997 | Harding |
| D379,516 S | 5/1997 | Rutter |
| 5,628,765 A * | 5/1997 | Morita ................ 606/182 |
| 5,666,966 A * | 9/1997 | Horie et al. ............. 600/573 |
| 5,730,753 A | 3/1998 | Morita |
| 5,741,288 A | 4/1998 | Rife |
| 5,857,983 A | 1/1999 | Douglas et al. |
| 5,868,772 A | 2/1999 | LeVaughn et al. |
| 5,872,713 A | 2/1999 | Douglas et al. |
| 5,879,311 A * | 3/1999 | Duchon et al. ............ 600/583 |
| 5,916,230 A | 6/1999 | Brenneman et al. |
| 5,951,492 A | 9/1999 | Douglas et al. |
| 5,951,582 A | 9/1999 | Thorne et al. |
| 5,954,738 A | 9/1999 | LeVaughn et al. |
| 5,971,941 A | 10/1999 | Simons et al. |
| 6,022,366 A | 2/2000 | Schraga |
| 6,027,459 A | 2/2000 | Shain et al. |
| 6,045,567 A | 4/2000 | Taylor et al. |
| 6,156,051 A | 12/2000 | Schraga |
| 6,206,856 B1 * | 3/2001 | Mahurkar ................ 604/195 |
| 6,287,265 B1 * | 9/2001 | Gleason ................ 600/573 |

FOREIGN PATENT DOCUMENTS

| | | |
|---|---|---|
| EP | 0449525 A1 | 2/1991 |
| EP | 0595148 A1 | 4/1994 |
| EP | 0894471 A2 | 3/1999 |
| WO | WO 97/42886 | 11/1997 |
| WO | WO 02/43591 A2 | 6/2002 |
| WO | WO 02/036010 A1 | 10/2002 |

OTHER PUBLICATIONS

Bayer, "Microlet" lancing device; 2 pgs.
Bayer, "Vaculance" lancing device; 1 pg.
Bechton-Dickinson, "Autolance" lancing device; 2 pgs.
Lifescan/Johnson & Johnson, "Penlet Plus" lancing device; 2 pgs.
Lifescan, "Penlet II" lancing device; 2 pgs.
Palco, "Auto-Lancet" lancing device; 2 pgs.
Roche, "Autoclix" lancing device; 2 pgs.
Roche, "Soft Touch II" lancing device; 1 pg.
Sutor, A., et. al., Bleeding From Standardized Skin Punctures, J.Cl.P., vol. 55, pp. 542-550 (1971).

* cited by examiner

SINGLE USE DEVICE FOR BLOOD MICROSAMPLING

CROSS-REFERENCE TO RELATED APPLICATION

This application claims the benefit of U.S. Provisional Pat. Application Ser. No. 60/353,917, filed Jan. 31, 2002, the entirety of which is hereby incorporated herein by reference for all purposes.

BACKGROUND OF THE INVENTION

1. Field of the Invention

The present invention relates generally to the field of lancing devices for sampling of blood or other body fluids, and more particularly to a single-use lancing device that prevents re-use.

2. Description of Related Art

Samples of blood must sometimes be collected from a human or animal subject. For example, many diabetics must periodically monitor their blood glucose level by collecting a small blood sample from their fingertip, forearm, or other body part, and chemically testing the blood sample. Small blood samples are also commonly collected prior to accepting a donor's blood at blood drives, to determine the donor's blood type and to screen potential donors for anemia or other conditions.

Lancing devices are commonly used to pierce the skin of a subject for sampling of blood, interstitial fluid, and/or other bodily fluids. Typically, a lancing device incorporates a spring-driven lancet and some type of triggering mechanism to release energy stored in the spring to drive the sharp edge or point of the lancet to penetrate the subject's skin. Various mechanisms also are known for limiting the travel of the lancet to control the depth of penetration of the lancet point into the skin, thereby minimizing trauma to the subject. However, many known depth-adjustment mechanisms are complex to manufacture and use, and/or have multiple components engaged between the lancet tip and the depth control element, thereby limiting the accuracy of depth control due to tolerance "stacking".

The risks of disease transmission due to transfer of blood and other bodily fluids are well known. One known manner of disease transmission is by reuse of needles or other sharp objects that have been contaminated with the blood of another subject. Re-use of a lancing device on different subjects, unintentionally or otherwise, could result in infection of the subsequent subjects through this transmission mechanism.

Thus, it has been found that needs exist for an improved lancing device that prevents intentional or accidental re-use. Needs further exist for a simple and accurate depth control mechanism for a lancing device. It is to these and other needs that the present invention is primarily directed.

SUMMARY OF THE INVENTION

Briefly described, in its preferred embodiments, the present invention relates generally to an improved lancing device. In example embodiments, the lancing device of the present invention prevents reuse after a single lancing action to prevent potential bloodborne disease transmission. In addition, example embodiments of the device of the present invention permit the user to adjust the penetration depth of the lancet.

In one embodiment, the present invention is a single-use lancing device. The device preferably includes a housing having a first end, a second end, and a chamber between the first and second ends. The first end of the housing preferably defines a lancet opening, and the housing preferably also includes at least one internal shoulder and a flange extending across at least a portion of the chamber. A lancet is preferably translationally mounted within the chamber of the housing for movement between a cocked position and a lancing position. The lancet has a lancet tip for passage through the lancet opening of the housing in the lancing position, and at least one finger for engaging the internal shoulder of the housing after firing to prevent reuse. A spring is preferably engaged between the lancet and the flange of the housing to drive the lancet from the cocked position toward the lancing position upon firing of the lancing device. A cocking arm is preferably connected to the lancet, and preferably includes at least one fin for releasable engagement with the flange of the housing to constrain the lancet in the cocked position.

In another embodiment, the present invention is a single-use lancing device including a spring-driven lancet that is translationally mounted within a housing. The lancet preferably includes at least one resilient finger extending outwardly therefrom, each finger being engageable within a cooperating recess formed in the housing to prevent re-use of the lancing device.

Another embodiment of the present invention is a lancing device including a housing having a first end, a second end, and at least one side wall defining a chamber between the first and second ends. A lancet is preferably translationally mounted within the chamber of the housing. A spring is preferably engaged between the lancet and the housing to drive the lancet from a cocked position toward a lancing position upon firing of the lancing device. A cocking arm is preferably connected to the lancet, the cocking arm preferably having at least one fin for releasable engagement with the housing to constrain the lancet in the cocked position. The device preferably also includes a depth-adjustment knob for contacting the housing to limit the travel of the lancet at the lancing position.

These and other features and advantages of representative embodiments of the present invention are described herein with reference to the drawing figures.

BRIEF DESCRIPTION OF THE DRAWING FIGURES

DETAILED DESCRIPTION

Figure 1:
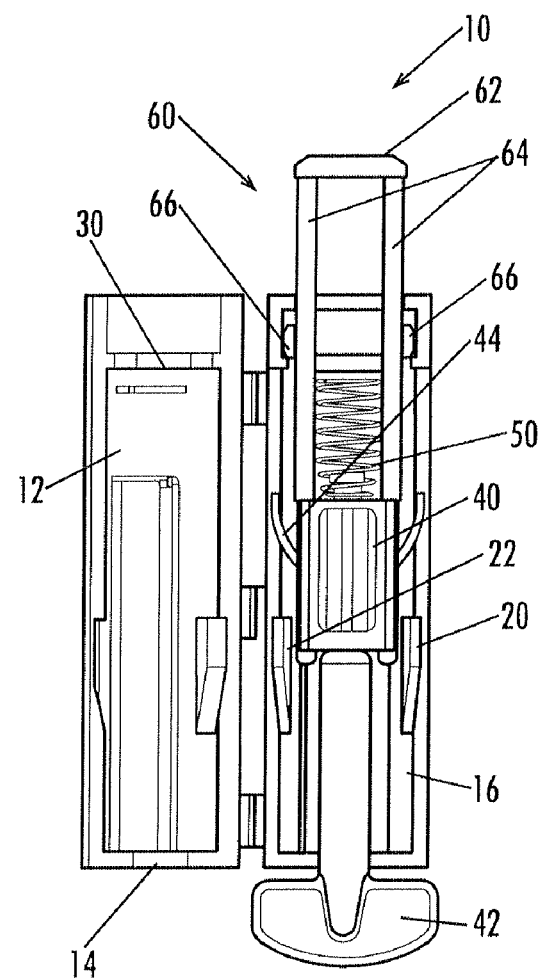
FIG. 1 is a front view of a lancing device according to one embodiment of the present invention, having its outer casing open to show internal components thereof.

Referring now to the drawing figures, in which like reference numbers refer to like parts throughout, preferred forms of the present invention will now be described by way of example embodiments. It is to be understood that the embodiments described and depicted herein are only selected examples of the many and various forms that the present invention may take, and that these examples are not intended to be exhaustive or limiting of the claimed invention. Also, as used in the specification including the appended claims, the singular forms "a," "an," and "the" include the plural unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

Figure 2:
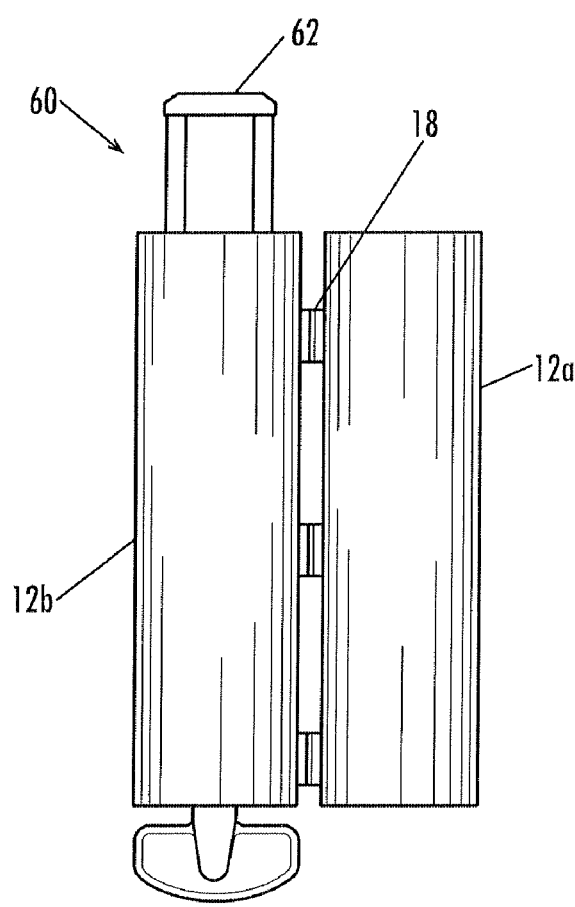
FIG. 2 is a rear view of the lancing device of FIG. 1.
Figure 3:
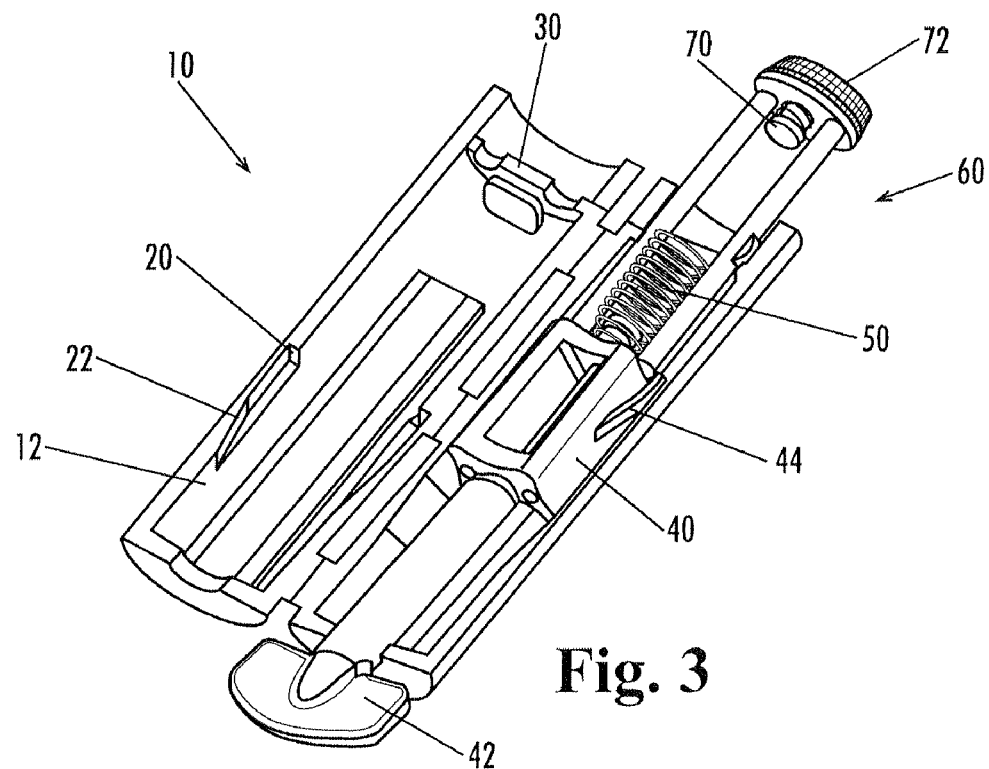
FIG. 3 is a perspective view of a lancing device according to another embodiment of the invention, also having its outer casing open to show internal components thereof.
Figure 4:
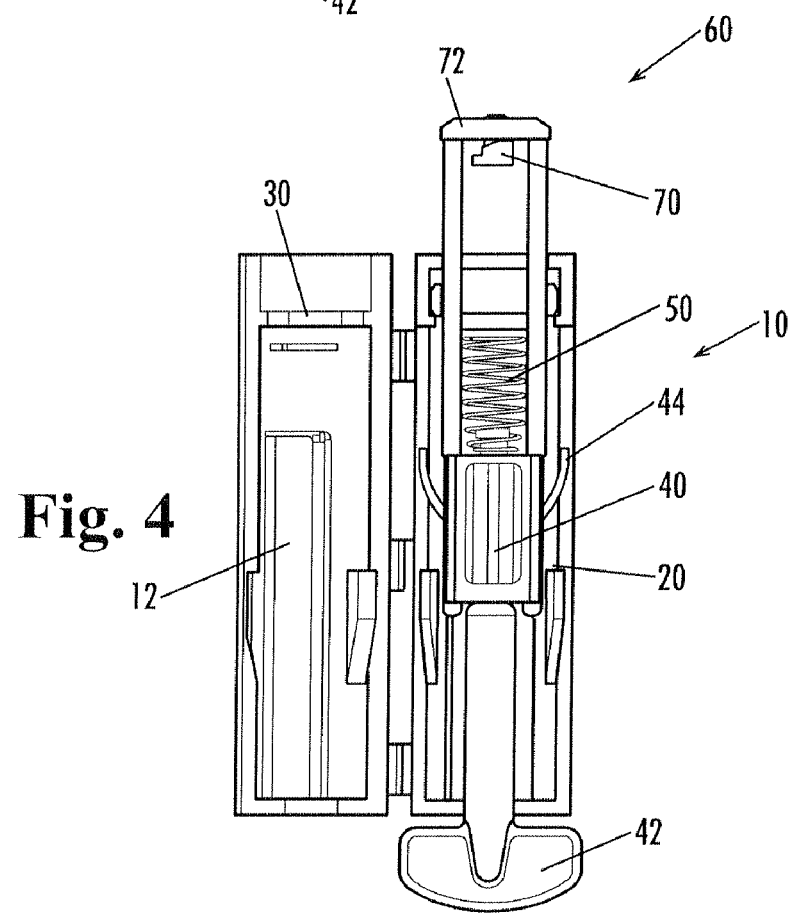
FIG. 4 is a front view of the lancing device of FIG. 3.
Figure 5:
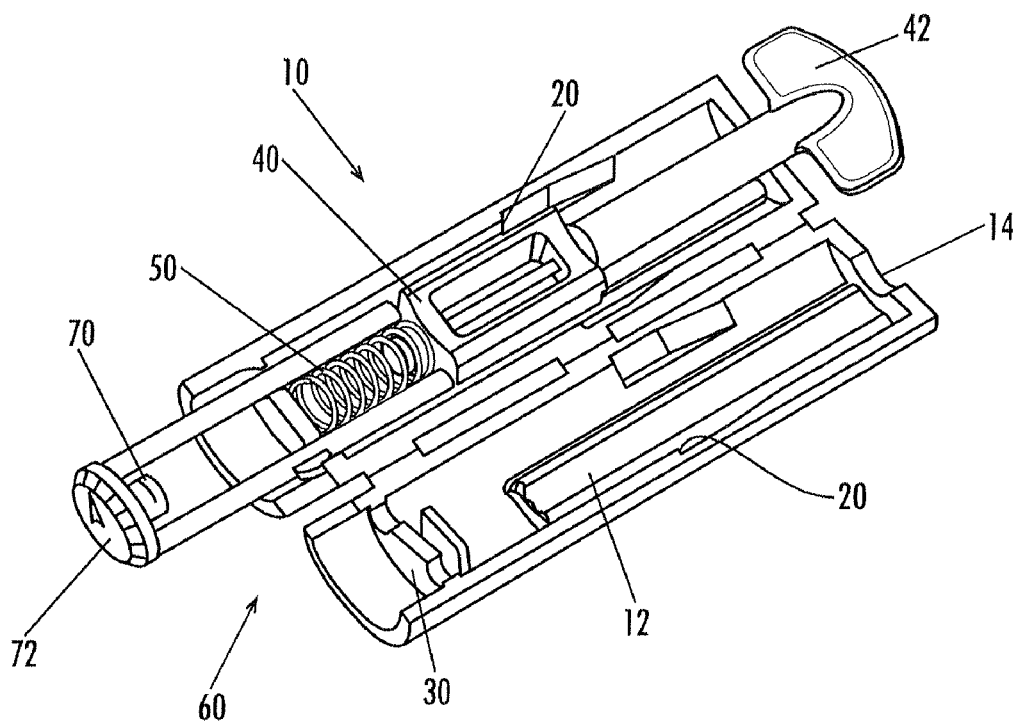
FIG. 5 is another perspective view of the lancing device of FIG. 3.
Figure 6:
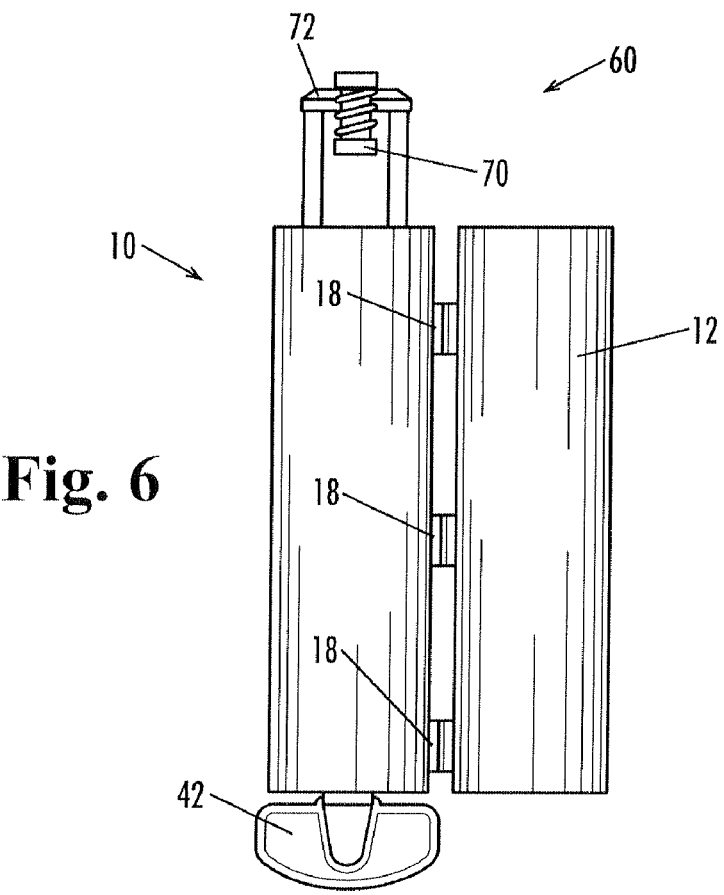
FIG. 6 is a rear view of the lancing device of FIG. 3.

With particular reference now to FIGS. 1-2, one embodiment of a lancing device 10 according to the present invention is shown. The device 10 preferably comprises a housing 12 having a first end defining a lancet opening 14 sized and shaped to permit at least a lancet tip portion of a lancet to pass therethrough. The first end of the housing optionally further comprises one or more raised rings or surfaces (unshown) for applying pressure against the subject's skin at the lancing site to enhance flow of blood and/or other body fluid to the skin surface for collection after lancing. The housing 12 preferably defines an internal chamber 16 for receiving a lancet upon assembly of the device 10. In the depicted embodiment, the housing 12 is generally cylindrical, and comprises a pair of half-shells 12a, 12b that are attached to one another upon assembly. To facilitate assembly, the half-shells 12a, 12b may be joined to one another by one or more hinges 18, and can comprise press fittings, clips, screws or other attachment means to securely engage the half-shells together upon assembly.

The housing 12 preferably further comprises at least one shoulder 20 on an internal face of a side wall bounding the chamber 16. The shoulder 20 preferably defines a face extending at approximately a right angle to the side wall of the housing 12 bounding the chamber 16. In the depicted embodiment, the shoulder 20 comprises one edge of a recess formed in the side wall, with the other edge of the recess smoothly inclined inwardly toward the first end of the housing 12. In an alternate embodiment, the shoulder comprises one edge face of a projection outward from the side wall, with the other edge of the projection smoothly inclined outwardly away from the first end of the housing 12. In the depicted embodiment, the housing 12 comprises a pair of shoulders 20 arranged on opposite sides of the chamber 16, and formed by an opposed pair of recesses 22 in the inside face of the sidewall of the housing 12. In alternative embodiments, three, four or more shoulders 20 are provided in spaced locations about the periphery of the chamber 16, or a single continuous shoulder 20 is provided extending about all or a portion of the periphery of the chamber.

The housing 12 preferably further comprises one or more flanges 30 extending from the sidewall of the housing. In the depicted embodiment, the flange 30 extends inwardly from the interior face of the sidewall of the housing 12 proximal the second end of the housing, forming the upper boundary of the chamber 16. In alternate embodiments, the one or more flanges extend outwardly from the exterior face of the sidewall of the housing. In the depicted embodiment, the flange 30 is formed by two generally semi-circular halves, one half of the flange formed into each half-shell 12a, 12b of the housing. In example embodiments, the housing is formed of plastic or other moldable material, as by injection molding or other plastics manufacturing technique, as a one-piece, unitary molding.

The lancing device 10 preferably further comprises a lancet 40 translationally mounted within the chamber 16 defined by the housing 12 upon assembly. The lancet 40 preferably comprises a body portion sized and shaped to slide freely between a cocked position and a lancing position within the chamber 16 without significant rotation or pivoting. The lancet 40 further comprises a lancet tip having a sharp point or edge for piercing the subject's skin at the lancing site to form a wound from which blood or other body fluids can be collected. In the assembled device 10, the lancet tip extends from the body of the lancet toward the first end of the housing 12 and extends through the lancet opening 14 (the lancing position) upon firing of the device. A sterility cap 42 is preferably secured over the lancet tip to maintain sterility of the lancet tip until the device is to be used. The sterility cap 42 preferably comprises one or more wings or other gripping surfaces to facilitate removal by twisting and separating the cap from the lancet body to expose the sharp lancet tip for use.

The lancet 40 preferably further comprises one or more fingers 44 for engaging the shoulder(s) 20 of the housing after firing to prevent reuse of the device. Preferably, one finger 44 is provided on the lancet 40 for each shoulder 20 of the housing, so that each finger engages a cooperating shoulder. Alternatively, two or more fingers 44 may engage a single shoulder 20 of the housing. In the depicted embodiment, two fingers 44 extend outwardly from opposite sides of the body of the lancet 40, each finger extending into one of the recesses 22 formed in the housing to engage a shoulder 20 to prevent re-cocking the device after a single firing. The provision of two or more fingers 44 evenly spaced about the periphery of the lancet 40 advantageously maintains the lancet along the central axis of the chamber 16 of the housing 12, and resists twisting and/or pivoting of the lancet within the housing as the device is cocked and fired. The one or more fingers 44 are preferably formed of a resilient material such as flexible plastic, and extend in a generally curved arc outwardly from the lancet body toward the second end of the housing when assembled, thereby maintaining outward pressure against the housing throughout the traverse of the lancet. The finger(s) 44 are preferably integrally formed with the lancet body, as by a single plastic molding. Alternatively, the finger(s) 44 are separately formed and attached to the lancet 40.

The lancing device 10 preferably further comprises a spring 50 or other means for propelling the lancet 40 from its cocked position to its lancing position. The spring 50 is preferably engaged between the lancet 40 and the housing 12. For example, in the depicted embodiment, one end of the spring 50 is secured to a retaining lug on the rear face of the body of the lancet 40, and the other end of the spring is attached against the flange 30 of the housing 12. The spring length and stiffness are preferably selected to drive the lancet 40 from the cocked position (depicted in FIG. 1) to the lancing position wherein the lancet tip extends through the lancet opening 14 a distance sufficient to pierce the subject's skin to a desired depth at a sampling site on the subject's fingertip or other body part against which the outside face of the first end of the housing 12 is pressed or placed. In further preferred forms, the spring 50 also serves to retract the lancet back into the housing after firing to prevent contact with the lancet tip. In the depicted embodiment, the natural (relaxed) length of the spring 50 is slightly less than would be required to position the lancet 40 in the lancing position with the lancet tip extending outside of the housing 12. Upon cocking and firing the device, the momentum of the lancet 40 stretches the spring 50 beyond its natural length, allowing the lancet to be propelled into the lancing position with the lancet tip extending outside of the housing 12. The spring 50 then retracts and reaches equilibrium at about its natural length, with the attached lancet 40 withdrawn into the housing 12 so that its tip is no longer exposed. In alternate embodiments, two or more springs are provided, for example a larger drive spring for propelling the lancet 40 from its cocked position to its lancing position, and a smaller retraction spring for withdrawing the lancet from the lancing position back into a retracted position fully within the housing.

The device 10 preferably further comprises a cocking arm 60 connected to the lancet 40 for cocking the device to arm the lancet for firing. In the depicted embodiment, the cocking arm 60 extends from the rear end of the lancet 40 (i.e., the end of the lancet opposite the lancet tip). In other embodiments, the cocking arm 60 is alternatively or additionally connected to one or more sides and/or the front end of the lancet 40. The cocking arm preferably includes a cocking grip 62 external of the housing 12 to permit the user to grip and pull the cocking arm, and at least one shaft 64 extending between the lancet 40 and the cocking grip 62. In the depicted embodiment, for example, two shafts 64 are provided between the lancet 40 and the cocking grip 62, each shaft attached to an opposite side of the rear end of the lancet. The provision of two or more evenly spaced shafts 64, or a single shaft located centrally, advantageously imparts force to the lancet 40 in an even manner to prevent undue twisting and/or pivoting of the lancet within the housing 12 as the device is cocked.

Each of the at least one shaft(s) 64 of the cocking arm preferably extend through a cooperating passage through the flange 30 of the housing 12, and further comprise(s) at least one fin 66 extending outwardly therefrom. As used herein, the term "fin" broadly encompasses any shaft segment presenting an expanded or irregular dimension relative to an adjacent shaft segment. The fin(s) 66 of each of the at least one shaft(s) 64 of the cocking arm preferably releasably engage the flange 30 to constrain the lancet 40 in the cocked position, once the device is cocked, until the device is triggered by the user. In the depicted embodiment, for example, one fin 66 extends outwardly from each shaft 64 a distance sufficient to provide an interference fit within a cooperating passage through the flange 30. The interference between the fin(s) 66 and the flange 30 is not so great as to prevent a user from easily cocking the device by grasping the cocking grip 62 between the thumb and forefinger and pulling away from the housing 12 to retract the fin(s) through the passages in the flange 30, but is sufficient to resist the force imparted on the lancet 40 by the spring 50 when the device is cocked. The device 10 then remains cocked until triggered by the application of light finger pressure to the cocking grip 62, whereupon the fin(s) are forced back through the passages in the flange 30, releasing the lancet to be propelled by the spring 50 toward the lancing position.

FIGS. 3-6 show another embodiment of the device 10, further comprising a depth-control mechanism. The depth-control mechanism preferably comprises a depth-adjustment knob 70 mounted to the cocking arm 60 for contacting the housing 12 to limit the travel of the lancet 40 at the lancing position. For example, in the depicted embodiment, the depth-adjustment knob 70 extends from the cocking grip 62 inwardly toward the housing 12, and contacts the flange 30 of the housing to limit the travel of the lancet 40 at the lancing position. The depth-control mechanism preferably, further comprises an adjustment dial 72 having one or more indicia (visual, audible, tactile or otherwise) for allowing the user to select a desired penetration depth setting corresponding to a respective position of the depth-adjustment knob 70.

In an example embodiment, the depth-adjustment knob 70 extends from the adjustment dial 72 and includes a threaded portion engaged within a cooperating threaded passage through the cocking grip 62. In this manner, rotation of the adjustment dial engages the threaded connection to extend or retract the depth-adjustment knob 70. Markings on the depth-adjustment knob 70 and the cocking grip 62 indicate the distance the depth-adjustment knob extends beyond the cocking grip. As the depth-adjustment knob 70 is extended further through the cocking grip 62 toward the housing 12, the depth-adjustment knob contacts the flange 30 of the housing earlier in the travel of the lancet, resulting in a shallower depth of penetration of the lancet tip beyond the lancet opening. Conversely, as the depth-adjustment knob 70 is retracted further through the cocking grip 62 away from the housing 12, the depth-adjustment knob contacts the flange 30 of the housing later in the travel of the lancet, resulting in a deeper penetration of the lancet tip further beyond the lancet opening.

In use, the device 10 is preferably provided to the user in an uncocked state, wherein the spring 50 is substantially relaxed, the lancet 40 is positioned with the fingers 44 between the recesses 22 and the flange 30, and the fins 66 are positioned on the internal side of the flange 30 within the chamber 16 of the housing 12. The sterility cap 42 is removed prior to use by gripping its wings, twisting and lightly pulling. The device is cocked by grasping the cocking grip and pulling it away from the housing 12 until the fins 66 are drawn through the passages in the flange 30. Interference between the fins 66 and the flange 30 constrains the device in the cocked position, with the spring 50 in compression. The lancet opening 14 at the first end of the housing 12 is pressed against the skin of the subject at the intended lancing site, preferably with the lancet's direction of travel oriented generally perpendicular to the skin surface. The device is triggered by pressing the cocking grip 62 toward the housing 12, pushing the fins 66 back through the passages in the flange 30 and thereby releasing the lancet 40 to be driven by the spring 50 toward the lancing position. At the lancing position, the sharp lancet tip extends through the lancet opening 14 and penetrates the subject's skin to produce a wound from which blood or other body fluids may be sampled. If desired, the user may press or pump the lancing device 10 against the skin after lancing to enhance the flow of body fluids at the sampling site. After lancing, the spring 50 preferably retracts toward its relaxed position to draw the lancet tip back through the lancet opening 14 and into the chamber 16, where it is shielded against accidental contact. The fingers 44 of the lancet 40 extend into the recesses 22 formed in the interior surface of the housing 12 and abut against the shoulders 20 to prevent the device from being re-cocked and re-used, which could lead to potential bloodborne disease transmission. The entire device may then be disposed of.

Embodiments of the device that include a depth-control mechanism are optionally adjusted to the desired piercing depth prior to triggering. For example, in the embodiment depicted in FIGS. 3-6, the user turns the depth-adjustment dial 72 using the indicia provided thereon as a guide, to extend or retract the depth-adjustment knob 70 to the position corresponding to the desired depth of penetration. When the device 10 is triggered, the depth-adjustment knob 70 contacts the flange 30 to limit the travel of the lancet 40, thereby limiting the depth of penetration of the lancet tip into the subject's skin at the lancing site.

While the invention has been described in its preferred forms, it will be readily apparent to those of ordinary skill in the art that many additions, modifications and deletions can be made thereto without departing from the spirit and scope of the invention.

What is claimed is:

1. A single-use lancing device comprising:
    a housing having a first end, a second end, and a chamber between said first and second ends, the first end of said housing defining a lancet opening, said housing further comprising at least one internal shoulder and a flange extending across at least a portion of the chamber;
    a lancet translationally mounted within the chamber of said housing for movement between a cocked position and a lancing position, said lancet having a lancet tip for passage through the lancet opening of said housing in the lancing position, and at least one finger for engaging the internal shoulder of said housing after firing to prevent reuse;
    a spring engaged between said lancet and the flange of said housing to drive said lancet from the cocked position toward the lancing position upon firing of the lancing device; and
    a cocking arm connected to said lancet, said cocking arm comprising a pair of shafts, a first end of each shaft connected to opposed sides of said lancet, and a second end of each shaft connected to a cocking grip, each shaft comprising a fin extending outwardly therefrom for releasable engagement with the flange of said housing to constrain said lancet in the cocked position.

2. The single-use lancing device of claim 1, wherein said cocking arm further comprises a depth-adjustment knob for contacting the flange of said housing to limit the travel of said lancet at the lancing position.

3. The single-use lancing device of claim 1, further comprising a sterility cap detachably mounted over the lancet tip.

4. The single-use lancing device of claim 1, wherein said housing comprises first and second half-shells hingedly joined to one another.

5. The single-use lancing device of claim 1, wherein the at least one internal shoulder of said housing is formed by an opposed pair of recesses within said housing between the first end of said housing and the flange.

6. The single-use lancing device of claim 5, wherein the at least one finger of said lancet comprises a pair of fingers extending outwardly and away from the lancet tip.

7. The single-use lancing device of claim 6, wherein each of said fingers is generally curved.

8. The single-use lancing device of claim 1, wherein said spring retracts the lancet to prevent the lancet tip from extending through the lancet opening of said housing after firing the lancing device.

9. A single-use lancing device comprising:
    a housing having a first end, a second end, and a chamber between said first and second ends, the first end of said housing defining a lancet opening, said housing further comprising at least one internal shoulder and a flange extending across at least a portion of the chamber;
    a lancet translationally mounted within the chamber of said housing for movement between a cocked position and a lancing position, said lancet having a lancet tip for passage through the lancet opening of said housing in the lancing position, and at least one finger for engaging the internal shoulder of said housing after firing to prevent reuse;
    a spring engaged between said lancet and the flange of said housing to drive said lancet from the cocked position toward the lancing position upon firing of the lancing device; and
    a cocking arm connected to said lancet, said cocking arm comprising a pair of shafts, a first end of each shaft connected to opposed sides of said lancet, and a second end of each shaft connected to a cocking grip, each shaft comprising a fin extending outwardly therefrom for releasable engagement with the flange of said housing to constrain said lancet in the cocked position, wherein said cocking arm further comprises a depth-adjustment knob for contacting the flange of said housing to limit the travel of said lancet at the lancing position.

10. The single-use lancing device of claim 9, further comprising a sterility cap detachably mounted over the lancet tip.

11. The single-use lancing device of claim 10, wherein the shafts extend through the flange and out of the second end of the housing and the fins releasably engage the flange in the cocked position to constrain the lancet in the cocked position.

12. The single-use lancing device of claim 9, wherein said housing comprises first and second half-shells hingedly joined to one another.

13. The single-use lancing device of claim 9, wherein the at least one internal shoulder of said housing is formed by an opposed pair of recesses within said housing between the first end of said housing and the flange.

14. The single-use lancing device of claim 13, wherein the at least one finger of said lancet comprises a pair of fingers extending outwardly and away from the lancet tip.

15. The single-use lancing device of claim 14, wherein each of said fingers is generally curved.

16. The single-use lancing device of claim 9, wherein said spring retracts the lancet to prevent the lancet tip from extending through the lancet opening of said housing after firing the lancing device.

17. A single-use lancing device comprising:
    a housing having a first end, a second end, a chamber between the first and second ends, and a flange extending across at least a portion of the chamber, the first end of the housing defining a lancet opening;
    a lancet translationally mounted within the chamber of the housing for movement between a cocked position and a lancing position, the lancet having a lancet tip for passage through the lancet opening of the housing in the lancing position;
    a spring engaged between the lancet and the housing to drive the lancet from the cocked position toward the lancing position upon firing of the lancing device; and
    a cocking arm comprising a cocking grip disposed outside of the housing, at least one shaft extending through the housing and connecting the cocking grip to the lancet, and at least one fin for releasable engagement with the housing to constrain the lancet in the cocked position, wherein the cocking grip can be grasped and moved to retract the lancet to the cocked position and to charge the spring, and wherein in the cocked position the fin releasably engages the housing with an interference fit to constrain the lancet in the cocked position.

18. The single-use lancing device of claim 17, wherein the shaft extends through the flange and out of the second end of the housing, the fin is disposed on and extends outwardly from the shaft, and the fin releasably engages the flange in the cocked position to constrain the lancet in the cocked position.

19. The single-use lancing device of claim 18, wherein the fin is on a first-end side of the flange when the lancet is in the lancing position and on a second-end side of the flange when the lancet is in the cocked position, wherein when the cocking grip is moved to retract the lancet toward the cocked position the fin comes into contact with the flange and in response thereto the cocking arm deflects to allow the fin past the flange and into the releaseable engagement, and wherein the releaseable engagement of the fin and the flange constrains the lancet in the cocked position until a force is applied to the cocking grip sufficient to cause the shaft to deflect and release the fin from engagement with the flange to fire the lancing device.

20. The single-use lancing device of claim 18, wherein the spring is engaged between the lancet and the flange and is compressed therebetween upon retraction of lancet to cocked position.

21. The single-use lancing device of claim 17, wherein the cocking arm comprises two of the shafts connecting the cocking grip to the lancet, the shafts are generally parallel to each other and connected to opposed sides of the lancet and of the cocking grip, each of the shafts having one of the fins extending outwardly therefrom for releasable engagement with the housing to constrain the lancet in the cocked position.

22. The single-use lancing device of claim 21, wherein the spring is disposed between the two shafts.

* * * * *